United States Patent [19]

Shuman

[11] 4,327,740
[45] May 4, 1982

[54] INCENTIVE SPIROMETER

[76] Inventor: Clyde Shuman, 25 Crescent Rd., Neffs, Pa. 18049

[21] Appl. No.: 95,374

[22] Filed: Nov. 19, 1979

[51] Int. Cl.³ .............................................. A61B 5/08
[52] U.S. Cl. ..................................... 128/728; 272/99; 92/45
[58] Field of Search ....................... 128/725, 727, 728; 272/99; 92/34, 45

[56] References Cited

U.S. PATENT DOCUMENTS

| | | | |
|---|---|---|---|
| 3,442,005 | 5/1969 | Langlet et al. ..................... | 92/45 X |
| 3,467,078 | 9/1969 | Bird et al. ............................ | 128/728 |
| 4,233,990 | 11/1980 | Yardley ................................ | 128/728 |
| 4,241,740 | 12/1980 | Brown ................................. | 128/728 |

FOREIGN PATENT DOCUMENTS

| | | | |
|---|---|---|---|
| 436569 | 1/1912 | France ................................. | 128/728 |
| 267933 | 6/1927 | United Kingdom ................... | 272/99 |
| 195037 | 6/1967 | U.S.S.R. ............................... | 128/728 |

*Primary Examiner*—Lee S. Cohen
*Attorney, Agent, or Firm*—Synnestvedt & Lechner

[57] ABSTRACT

A volume-type incentive spirometer for respiration therapy is disclosed. The spirometer includes a central tubular support on which is mounted a collapsible bellows-like chamber. Fluid communication is provided between the support and the interior of the chamber and, further, between the support and a patient. The collapsible chamber includes a top plate by which the chamber is mounted on the support, a bottom plate for biasing the collapsible chamber to an open position, and an intervening flexible, readily collapsible side wall joining the top and bottom plates. The collapsible chamber or the collapsible chamber and support member may be disposable. The spirometer provides respiratory exercise so that alveolar inflation is assured.

16 Claims, 10 Drawing Figures

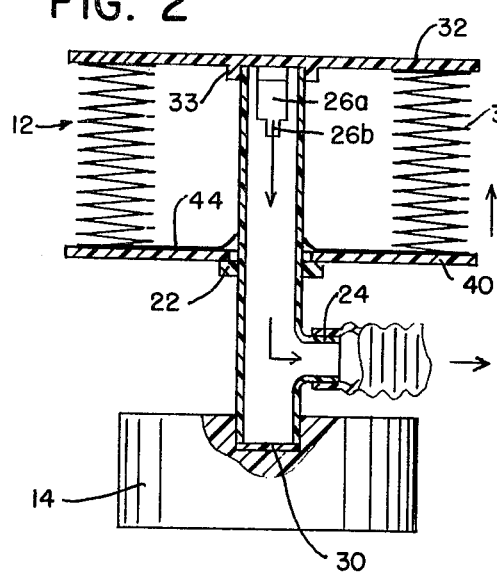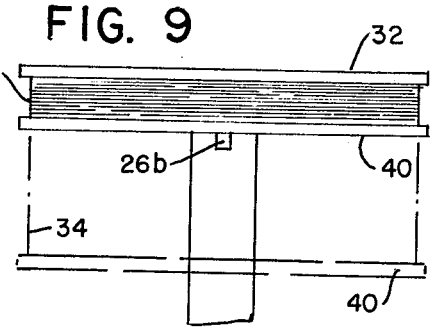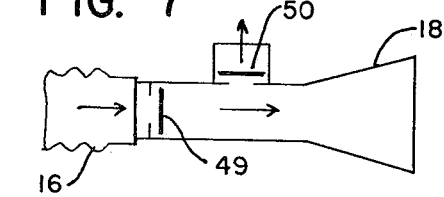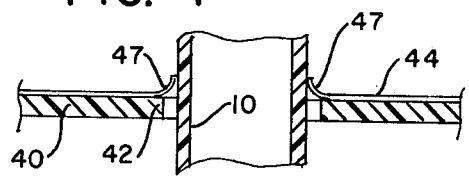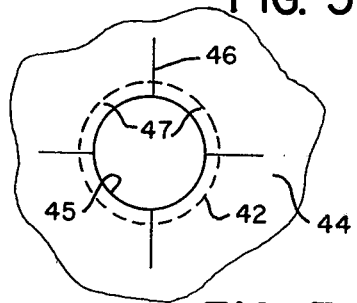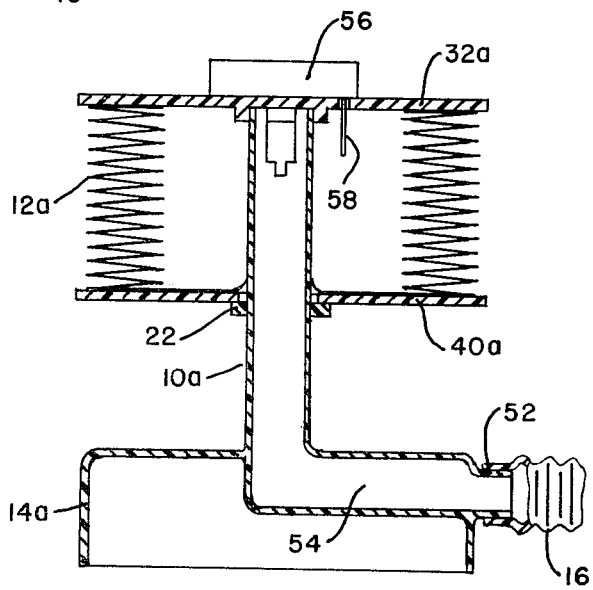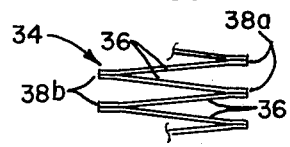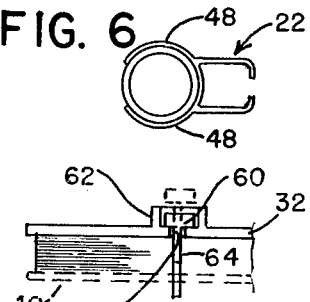

INCENTIVE SPIROMETER

FIELD OF THE INVENTION

This invention relates to respiratory exercising devices and particularly to incentive spirometers used for post-operative patient care.

BACKGROUND OF THE INVENTION

Often patients who have undergone abdominal and thoracic surgery experience a reduced respiratory function. This is believed to occur because anesthetics, analgesics, pain and dressings affect the normal deep breathing reflex. This alteration of the normal pattern can lead to alveolar collapse that, if not reversed, can cause a substantial reduction in the amount of oxygen absorbed by the patient's blood stream.

To combat this problem, respiratory exercisers have been proposed that are designed to make the patient breathe deeply voluntarily.

There are basically two forms of incentive exercising devices that have been proposed. In one category are the types of exercisers that indicate the flow rate of the patient's inhalation, as illustrated in U.S. Pat. Nos. 4,037,836, 4,060,074, 4,086,919, and 4,138,105. Commonly, these designs employ at least one lightweight hollow sphere that is drawn upwardly in a column when the patient inhales. The vertical position of the sphere and the number of spheres raised gives an indication of the flow rate of the inhaled air. A problem with such exercisers is that the alveolar reinflation is primarily a function of the volume of air inspired by the patient and to determine that volume, using these first-mentioned exercisers, it is necessary for the patient, or an observer, to determine the time that the indicator is at its uppermost position so that, usually by reference to a chart giving flow rates and times, the inspired volume can be determined. This is disadvantageous because the patient is often unable or unwilling to time the inhalation and the timing and calculation must be performed by a person who must take time from other duties.

In order to overcome this disadvantage, a second category of spirometer has been proposed in which the volume of each inspiration is directly indicated. Spirometers in this category are illustrated in U.S. Pat. Nos. 3,754,546 and 4,096,855, both of which show devices employing a piston, within an enclosure, for indicating inspiration volume. These designs are relatively expensive to manufacture and this makes them unattractive for use as a disposable item used only by one patient.

Recently, another form of the volume-type spirometer has been proposed. In this design, a collapsible blow-molded bellows is supported in a five-sided box. The patient inhales through a tube that is in fluid communication with the interior of the bellows. The collapse of the bellows, upon inspiration by the patient, gives a measure of the volume of air drawn in by the patient. This design is relatively bulky and difficult to collapse and thus presents shipping problems.

SUMMARY OF THE INVENTION

It is an object of this invention to provide an incentive spirometer that provides a reliable indication of the volume of air inhaled by the patient.

It is also an object of the invention to provide a low-cost, disposable incentive spirometer that can be easily packaged.

It is a further object of the invention to provide an incentive spirometer that can be utilized with patients whose respiratory capability is severely impaired.

These and other objects of the invention are achieved by a spirometer that includes a central support member for supporting a collapsible chamber. The support member incorporates means to provide fluid communication between the interior of the collapsible chamber and the user. The collapsible chamber has a side wall that offers substantially no resistance to collapse.

DESCRIPTION OF THE DRAWINGS

FIG. 2 is a side-sectional view of the assembled spirometer of FIG. 1.

FIG. 3 is a fragmentary, enlarged view of a preferred collapsible side wall construction for the collapsilbe chamber.

FIG. 4 is an enlarged cross-sectional view showing a preferred form of sealing arrangement for the movable plate of the collapsible chamber relative to the support member.

FIG. 5 is a fragmentary, enlarged top view of the seal shown in FIG. 4.

FIG. 6 is an illustration of a stop member that can be used for setting the volume of air to be inspired by a patient.

FIG. 7 is a schematic view of a preferred form of mouthpiece.

FIG. 8 is a cross-sectional view of another form of applicant's spirometer design.

FIG. 9 is a side elevation showing the collapsible chamber collapsed at or near its maximum extent.

FIG. 10 illustrates a goal achievement indicator for showing the full collapse of the collapsible chamber.

DESCRIPTION OF THE PREFFERED EMBODIMENT

Figure 1:
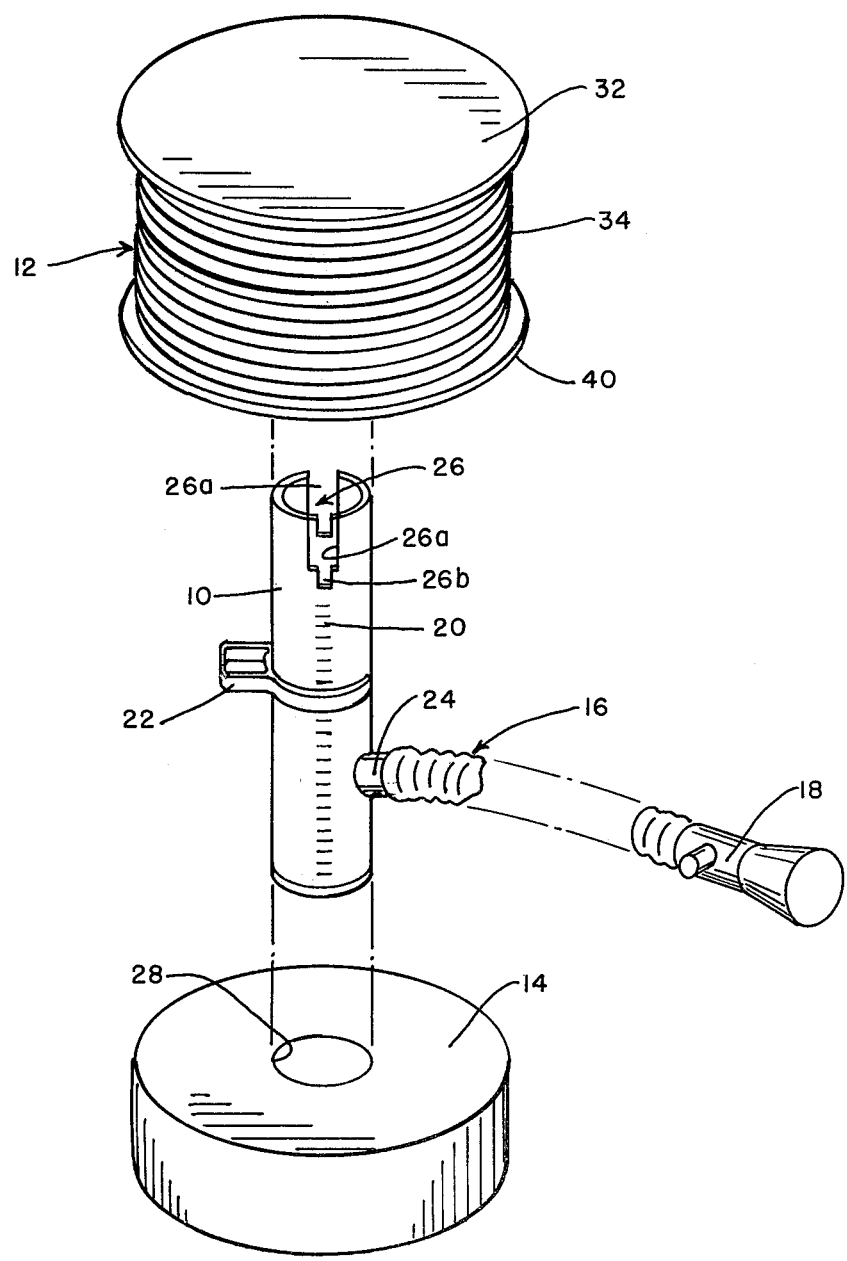
FIG. 1 is an exploded perspective view of the components of a preferred embodiment of spirometer.

Referring to FIG. 1, applicant's spirometer comprises, in the preferred embodiment, substantially four parts, including a rigid tubular support member 10, a collapsible inspiration volume measuring chamber 12 surrounding the support 10, a base 14 for holding the support 10 and a fluid conduit 16 terminating in a mouthpiece 18 for providing fluid communication between the spirometer and the patient.

The support member 10 may be provided with a plurality of graduation marks 20 and an adjustable stop member 22, the functions of which will be described below.

Means are provided for establishing a fluid flow path from the interior of the collapsible chamber to the patient. In the arrangement shown in FIGS. 1 and 2, the tube 10, at its upper end, has ports 26 for establishing fluid communication between the interior of the tube and the interior of chamber 12. As shown, the ports 26 can comprise two diametrically opposed grooves 26a formed in the top of the tube 10. In the preferred form, each of the grooves 26a further includes a smaller relief or safety port 26b, the function of which is later explained.

The support member 10 also includes port means for providing fluid communication with the interior of the support. In the preferred design, such means comprises a stub conduit 24 that provides a means for receiving one end of the conduit 16 and that is in fluid communication with the interior of the tubular support 10.

In the form shown in FIG. 1, the support member 10 is held in an upright position by a relatively heavy base 14 that has a bore 28 for receiving the bottom portion of the tube 10. As shown in FIG. 2, the tube 10 preferably has an imperforate bottom wall 30. In this embodiment, the tube 10, the chamber 12 and conduit 16 are supplied as disposable, single-use parts of the apparatus.

Referring to FIGS. 1 and 2, the collapsible inspiration volume measuring chamber 12 is fitted on the upper end of the tube 10. In the preferred arrangement, the chamber 12 includes a substantially rigid, substantially fluid-impervious top plate or end wall 32 on the lower surface of which is a centrally located annular boss 33 that receives the upper end of the tube 10 in a relatively snug-fitting relationship. The chamber 12 further comprises a continuous, collapsible, tubular side wall 34 that is imperforate and that is sealed at its top to the bottom surface of the plate 32. Such sealing can be by means of heat sealing or adhesives, for example.

Preferably, the side wall 34 is of a construction that offers substantially no resistance to longitudinal collapse and that collapses in a reasonably orderly, flat fashion.

One form of such construction of the wall 34 is shown in detail in FIG. 3. The wall comprises a plurality of flat leaves 36 that are arranged in a substantially stacked relationship. It should be realized that the perimeteral configuration of the chamber 12 is not material to the invention. However, it has been found convenient to use a circular configuration, in which case, the chamber is essentially cylindrical. If the cylindrical configuration is used, then each of the leaves 36 comprises an annulus. The annuli 36 can be made from a wide variety of materials, such as rubbers, plastics or treated cloths; however, the preferred material is a flexible sheet or film of a synthetic polymeric material, for example, a polyethylene, a vinyl, or a polyvinyl chloride film having a thickness in the range of about 0.004 to about 0.012 inch. Preferably, the material is thermoplastic. The annuli are joined together alternately at their outer and inner edges by continuous circumferential welds 38a and 38b respectively, thereby forming a substantially bellows-like structure. The welds extend between top and bottom surfaces of adjacent leaves at alternate inside and outside edge locations and can be formed by heat or solvent welding techniques, as well as by adhesives. Conveniently, radio frequency welding is used to join the annuli 36 together at alternate edges. The alternation of joined layers can be achieved by interleaving sheets of a high-melting-point material, for example, Teflon, between adjacent leaves 36 at alternate inside and outside locations. Protective boots for hydraulic machinery have been manufactured by this technique for many years and it is not believed that further explanation or detail is necessary with respect to this process.

It should be realized that other techniques can be used for forming walls 34 having the desired characteristics of offering substantially no resistance to collapse and an orderly, flat collapse. For example, the wall could be made by plastisol dipping to form a continuous corrugated side wall. Again, a flexible synthetic thermoplastic material or a rubber could be used. Side walls formed by dipping should be relatively thin so that the finished wall does not exhibit any substantial resistance to collapse. For this reason, side wall thicknesses of from about 0.015 to about 0.030 inch are appropriate.

The advantages of using these types of wall construction are that the wall offers substantially no resistance to collapse and thus the unit can be used with patients whose respiratory ability is severly impaired. The weight of bottom plate 40 provides the only resistance to upward collapse of the chamber 12. In addition, the sections 36 fold flat against each other when the chamber is collapsed. Thus, the chamber 10 readily assumes a flat condition for shipping and this simplifies packing.

The wall 34 is attached at its lower end and sealed to a substantially rigid plate 40 by securing means such as the disc-shaped sheet 44. The plate 40 includes a substantially centrally located aperture 42, somewhat greater in size than the area of the horizontal cross section of the support 10, whereby the plate 40 encircles the tube 10 and can move vertically along the tube 10. The plate 40 has sufficient mass so that it acts as a biasing means to expand the collapsible wall 34 downwardly and thus maintain the chamber 12 in an open position.

As can be seen in FIGS. 4 and 5, the aperture 42 in the plate 40 is provided with a sliding fluid seal so that passage of the ambient air into the interior of the chamber 12 is substantially precluded when the chamber 12 is being collapsed by reason of the patient's inspiration of air from within the chamber. Many types of arrangements could be used to form a suitable movable seal. However, one form that has been found to be particularly useful to form a seal integrally with sheet 44 that may be formed of the same flat, flexible material as the leaves 36, for example, a flexible polyethylene sheet material. The sheet 44 is provided with an aperture 45, the diameter of which is somewhat less than the outer diameter of the tube 10. In order to allow the seal to be fit over the tube 10 and slide along that tube, it is desirable to provide one or more slits 46, thereby forming a plurality of flaps 47, so that the plate 40 can more relatively freely with respect to the tube 10.

In order to set the inspiration volume that a particular patient is expected to achieve, the starting position of the plate 40 can be adjusted by means of the stop member 22 that is shown positioned on the tubular support 10 in FIGS. 1 and 2 and that is shown in top view in FIG. 6. The stop member 22 is preferably of a resilient plastic material and includes bifurcations 48 that snap over the tube 10 with sufficient frictional engagement to support the plate 40. The graduations 20 provide a convenient manner of indicating the desired placement of the stop member 22. The graduations can be marked to indicate the volume of the chamber 12 for any given position of the stop member 22. In another mode of operation, the stop member 22 can be dispensed with and the inhalation volume noted merely from the height to which the plate 40 is drawn by the patient.

The fluid conduit 16 is preferably a flexible tube, such as the convoluted plastic tubing that is commonly used with respiratory devices. One end of the tube 16 fits on the stub conduit 24 and the other end is attached to a mouthpiece 18 which the patient uses. The mouthpiece may simply be a tube shaped to fit the mouth, or, referring to FIG. 7, the mouthpiece 18 may have a double check valve arrangement comprising an inlet check valve 49 and an outlet check valve 50. The valve 49 allows air to be drawn into the mouthpiece from the spirometer but prevents exhaled air from the patient to be passed back through the tube 16. The check valve 50 prevents ambient air from being drawn into the mouthpiece when the patient is inhaling, but allows air exhaled into the mouthpiece to pass into the ambient. Thus there is no need for the patient to remove the mouthpiece shown in FIG. 7 from his mouth to exhale or to cover an open exhalation port with a finger when inhaling. When the FIG. 7 form of mouthpice is used, the seal between plate 40 and support 10 must be of a type that allows air to re-enter the chamber, for example, under the flaps 47 which, after inhalation by the patient has ceased, allows the plate 40, by gravitational force, to pull the collapsed side wall 34 to an open position.

Referring to FIG. 8, instead of having the support member 10 separable from the base 14 as in the example illustrated in FIGS. 1 and 2, the base 14a can be formed integrally with the support tube 10a. The conduit 16 is assembled onto a nipple 52 that is formed integrally with the base 14a. The nipple 52 is in fluid communication with the hollow interior of the support member 10a by means of an integrally formed conduit 54. In this arrangement, it is believed preferable that just the collapsible chamber 12a and the conduit 16 with its associated mouthpiece may be disposable and that the base unit 14a with integral support be sterilizable for reuse. Alternatively, all of the parts of this design could be disposable.

Referring to FIG. 8, the total volume of air inhaled by a patient in a given period of time can be determined by the use of a counter 56 mounted on the top plate 32a. The counter 56 has an actuating member 58 extending downwardly through an opening in the plate 32a and is positioned to be engaged by the bottom plate 40a, each time the plate is drawn upwardly. By knowing the volume of the chamber 12 and the number of times the counter is actuated, the total volume of air inhaled by a patient over a period of time can be calculated.

Another form of indicator is shown in FIG. 10. Here, an indicator button 60 rests on the upper surface of the top plate 32. The button 60 is retained in position by an annular boss 62 that can be formed integrally on the plate 32. The button 60 includes a downwardly depending shank 64 that extends through a hole 66 in the plate. When the plate 40 is drawn upwardly at or near its maximum extent, plate 40 engages shank 64 and drives the button 60 upwardly. The shank 64 and hole 66 are sized so that there is little or no air leakage into the chamber 12.

In operation, once the spirometer is assembled, as shown in FIGS. 1 and 2, the patient inhales through the mouthpiece 18 and the reduced pressure is communicated through the conduit 16 to the hollow interior of the tubular support 10. From the interior of the support, the lowered pressure is communicated to the interior of the chamber 12 by means of the port or ports 26 at the top of the tube 10. The reduction of pressure within the chamber 12 causes the chamber to collapse as the pressure differential across the lower plate 40 causes the plate to rise vertically, once the upward force created by the differential is sufficient to overcome gravitational and frictional forces acting on plate 40. Assuming the patient has sufficient inspiratory capacity, the plate 40 continues to rise and the volume of the collapse can be noted by means of the graduations 20. When the chamber 12 is fully collapsed, as shown in FIG. 9, the bottom plate 40 will have traveled upwardly to a sufficient extent to continue to enclose ports 6a, but to uncover the relief ports 26b so that communication to ambient is established and the patient can continue to inhale, if he so desires. When the patient terminates the inhalation, the weight of the plate 40 draws the side walls 34 downwardly and thereby expands the chamber 12.

Applicant's design presents several advantages. The collapsible chamber 12 is easily collapsed, even under very low inhalation volumes. Also, inspiratory goals can be set very easily and inspiration volumes determined very easily. Further, the spirometer can be assembled quickly and easily from parts that are easily packaged in relatively small packages.

I claim:

1. A spirometer assembly comprising an elongate support; a hollow, collapsible, substantially fluid-tight chamber; means for mounting the chamber on the support in surrounding relationship thereto; means for biasing the collapsible chamber toward an open position when the collapsible chamber is mounted on the support; and means for providing fluid communication between the interior of the collapsible chamber and a patient when the collapsible chamber is biased toward an open position and between the patient and ambient when the collapsible member is in substantially a fully collapsed condition.

2. Apparatus as in claim 1 wherein the support is a rigid tubular member having means for providing fluid communication between the interior of the collapsible chamber and the interior of the tubular support at all stages of biasing of the chamber between open and fully collapsed condition and further having means for providing fluid communication between the interior of the tubular support and a patient when the collapsible chamber is biased toward an open position.

3. Apparatus as in claim 2 wherein the collapsible chamber comprises a first plate and means for securing the first plate in fixed relation on the support, a tubular, thin-walled, collapsible body section, one end of which is affixed to the first plate, and wherein the biasing means comprises a second plate affixed to the other end of the body section.

4. Apparatus as in claim 3 wherein the second plate has an opening slidably receiving the tubular support member.

5. Apparatus as in claim 4 wherein the opening in the second plate includes means for providing a sliding fluid seal between the support member and the opening in the second plate.

6. Apparatus as in claim 2 including stop means movably mountable on the support to limit the open position of the collapsible chamber and for setting the starting volume of the collapsible chamber.

7. Apparatus as in claim 1 wherein the collapsible chamber offers substantially no resistance to collapse.

8. Apparatus as in claim 7 wherein the collapsible chamber includes a side wall comprising a plurality of thin, stacked leaves joined together.

9. Apparatus as in claim 8 wherein the leaves are substantially flat and are joined together at alternate inside and outside edges.

10. Apparatus as in claims 8 or 9 wherein the leaves are of flexible thin-film material having a thickness of about 0.004 to about 0.030 inch.

11. An incentive spirometer comprising
a tubular support member forming a fluid conduit,
a collapsible, substantially fluid-tight chamber, said chamber including a first end wall, means on the first end wall for securing the collapsible chamber on the support member, a second end wall having an aperture slidably receiving the support member, and a continuous, flexible side wall joining the first end wall to the second end wall, means for providing fluid communication between the interior of the tubular support member and the interior of the collapsible chamber whereby a reduction in fluid pressure within the support member results in a reduction of fluid pressure within the collapsible chamber, and means for providing fluid communication between the interior of the tubular support member and a patient when the collapsible chamber is biased toward an open position and between the patient and ambient when the collapsible chamber is in a substantially fully collapsed condition.

12. Apparatus as in claim 11 and further including means for maintaining the support member in an upright position.

13. Apparatus as in claim 12 wherein the side wall offers substantially no resistance to longitudinal collapse.

14. Apparatus as in claim 13 wherein the side wall comprises a stacked array of leaves of a flexible sheet material.

15. Apparatus as in claim 14 wherein the leaves are substantially flat and are joined together at alternate inside and outside edges.

16. A spirometer assembly comprising an elongate support; a hollow, collapsible, substantially fluid-tight chamber; means for mounting the chamber on the support in surrounding relationship thereto; means for biasing the collapsible chamber toward an open position when the collapsible chamber is mounted on the support; means for providing fluid communication between the interior of the collapsible chamber and a patient when the collapsible chamber is biased toward an open position and between the patient and ambient when the collapsible chamber is in substantially a fully collapsed condition; and stop means movably mounted on said support to limit the open position of the collapsible chamber and for setting the starting volume of the collapsible chamber.

* * * * *